United States Patent [19]

Enjoji et al.

[11] Patent Number: 4,548,210
[45] Date of Patent: Oct. 22, 1985

[54] PROBE FOR ULTRASONIC-ECHO PLANIGRAPHIC IMAGING APPARATUS

[75] Inventors: Susumu Enjoji; Koji Saito, both of Tokyo, Japan

[73] Assignee: Tokyo Shibaura Denki Kabushiki Kaisha, Kawasaki, Japan

[21] Appl. No.: 290,401

[22] Filed: Aug. 5, 1981

Related U.S. Application Data

[63] Continuation of Ser. No. 10,596, Feb. 7, 1979, abandoned.

[51] Int. Cl.⁴ .............................................. A61B 10/00
[52] U.S. Cl. .................................................. 128/660
[58] Field of Search ....................... 128/653, 660–663, 128/691, 303 B; 604/264, 272, 273

[56] References Cited

U.S. PATENT DOCUMENTS 4,029,084  6/1977  Soldner ............................... 128/660
4,108,165  8/1978  Kopp et al. ......................... 128/660

Primary Examiner—William E. Kamm
Attorney, Agent, or Firm—Cushman, Darby & Cushman

[57] ABSTRACT

A probe for an ultrasonic-echo planigraphic imaging apparatus, which comprises a support whose bottom wall brought into contact with a human body is provided with a plurality of transducer elements egnidistantly arranged at least in one row lengthwise of the support, and which has a cavity extending partly across the support from one lengthwise lateral wall thereof; and a member which is detachably inserted into the cavity to define an opening for insertion of a puncturing cannula.

3 Claims, 7 Drawing Figures

PROBE FOR ULTRASONIC-ECHO PLANIGRAPHIC IMAGING APPARATUS

This application is a continuation of application Ser. No. 010,596 filed Feb. 7, 1979, now abandoned.

BACKGROUND OF THE INVENTION

This invention relates to a probe for ultrasonic-echo planigraphic imaging apparatus used when a puncturing cannula is inserted into the predetermined portion of a living human body as in biopsy.

In recent years, a blood vessel-imaging method is applied as important means for discovering morbid changes in the cerebrum, heart, abdominal organs and limbs. This method comprises the steps of inserting a puncturing cannula into the pancreatic duct or cystic duct of the above-mentioned sections of a human body to pour a contrasting mediums thereinto and carrying out the X-ray photography of the predetermined portions of said sections. Another important examining method is to aspirate a tissue of the organs of a human body such as a liver, kidney or tumor by means of a puncturing cannula.

In this case, it is very important to determine the exact position of that part of the organs or blood vessels which is to be pierced by a puncturing cannula in order to avoid the biopsy of an unnecessary tissue of the organs or the flow of contrast medium into the wrong tissue. Further, it will offer great advantage if the behavior of a puncturing cannula can be traced in real time which occurs during a period extending from a point of time at which the cannula begins to be inserted to a point of time at which said cannula reaches the tissue of the predetermined organ.

A planigraphic imaging apparatus utilizing ultrasonic waves is already used for the above-mentioned object. This ultrasonic-echo planigraphic imaging apparatus comprises a probe consisting of a plurality of electro-acoustic transducer elements which are linearly arranged at least in that portion of said probe which contacts the human body and whose adjacent ones are simultaneously operated.

The sectional plane of that portion of the human body which is to be inserted by the puncturing cannula is progressively scanned by ultrasonic beams supplied from the above-mentioned transducer elements. The resultant planigraphic image is indicated on the CRT of a display device.

A probe used to discover the position of the predetermined portion of a human body before the X-ray photography thereof has to be removed at the time of photography in order to prevent an unnecessary image of the probe itself from being indicated on the CRT of the display device.

There will now be described by reference to FIGS. 1a and 1b a conventional probe. The probe 1 comprises a support 4 provided with a plurality of transducer elements 3 arranged at least in one row on that side 2 of the probe 1 which made to contact a human body; and a guide slit 5 which extends lengthwise of the support 4 over the linearly arranged transducer elements 3 to guide the insertion of a puncturing cannula 6. The guide slit 5 has a V-shaped cross section which is gradually broadened from the human body-contacting side 2 of the support 4 toward the upper opposite side thereof. Accordingly, the puncturing cannula 6 is conducted from above the guide slit 5 into the predetermined portion of a human body. Where the puncturing cannula 6 reaches the prescribed position, the probe has to be removed from the human body for the reason previously given. During the removal, the conventional probe 3 provided with the above-mentioned guide-slit 5 unavoidably touches the puncturing cannula 6 already inserted into the human body. As a result, the direction in which the puncturing cannula 6 is inserted would probably be changed to injure an undesired portion of the human body. Further, once the puncturing cannula 6 is inserted through the guide slit 5 of the probe 1, an operator cannot freely change the direction in which the puncturing cannula 6 is to be inserted. Moreover, unless the operator applies a uniform force to the cannula 6, then there arises the undesired possibility of the cannula 6 being inserted in the wrong direction. With the conventional probe 1, therefore, high skill has been demanded for the accurate insertion of the cannula 6.

SUMMARY OF THE INVENTION

It is accordingly the object of this invention to provide a probe for an ultrasonic-echo planigraphic imaging apparatus, wherein the probe can be easily removed from the human body without touching the puncturing cannula already inserted into the predetermined portion thereof when the X-ray photography of said portion is undertaken under such condition.

BRIEF DESCRIPTION OF THE DRAWING

FIG. 1b is a sectional view on line Ib—Ib of FIG. 1a;

DESCRIPTION OF THE PREFERRED EMBODIMENTS

Figure 1A:
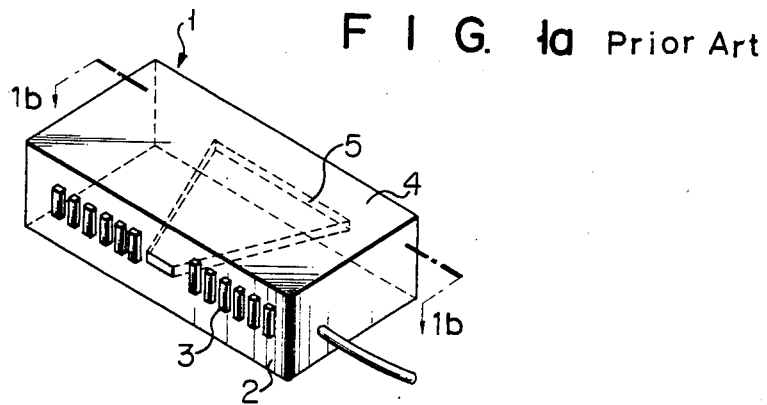
FIG. 1a is a perspective view of a prior art ultrasound probe.
Figure 1B:
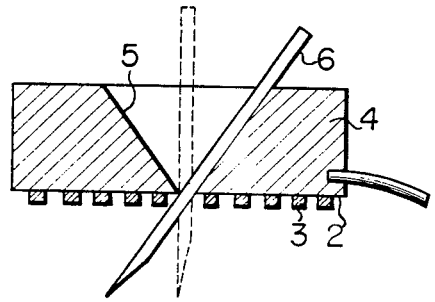
Figure 2:
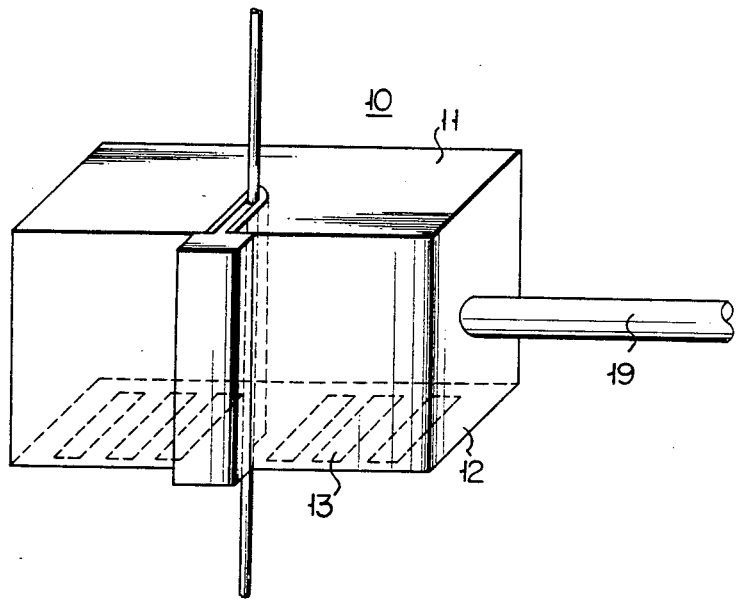
FIG. 2 is a perspective view of an ultrasound probe according to a first embodiment of this invention.

Referring to FIG. 2, reference numeral 11 denotes a parallelepiped support made of hardened resin. That side 12 of the support 11 which contacts a human body is provided with a plurality of electro-acoustic transducer elements 13 equidistantly arranged at least in one row lengthwise of the support 11.

Figure 3:
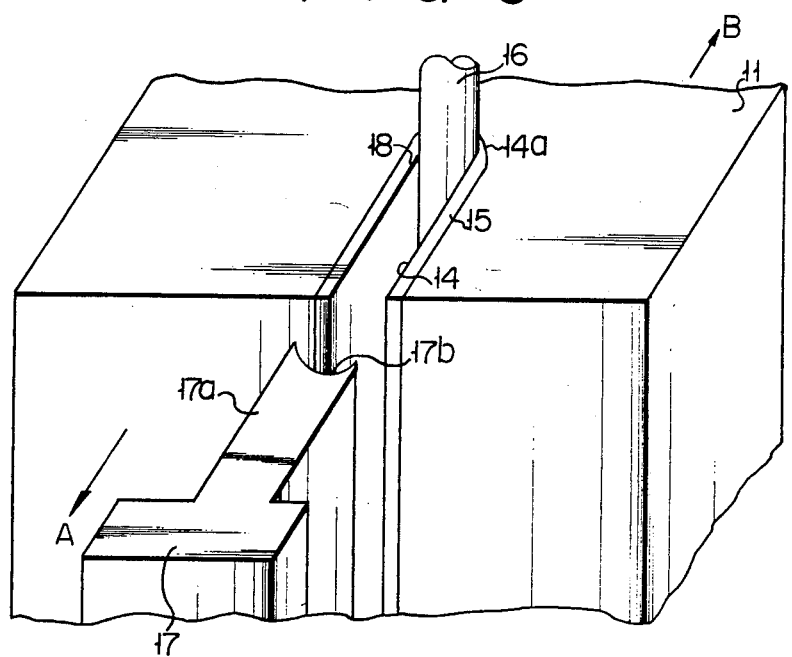
FIG. 3 is a partial enlarged view of the ultrasound probe of FIG. 2.

As indicated in greater detail in FIG. 3, a groove 14 is cut out in the support 11 which penetrates the upper and lower walls of the support 11 in a direction perpendicular to that side 12 of the support 11 which is made to contact a human body and extends partly across the support 11 in a horizontal direction at a prescribed distance from one of the lengthwise lateral walls of the support 11. The inner end portion of the groove 14 is provided with a semicircular recess to conform with the peripheral outline of a puncturing cannula 16. All the inner walls of the groove 14 are fitted with an electrically insulating layer 15. This electrically insulating layer 15 serves to insure the smooth insertion of the puncturing cannula 16 into the predetermined portion of the human body without touching the support 11 of the ultrasound probe 10.

Reference numeral 17 denotes a T-shaped adapter which is to be inserted into the groove 14. This adapter 17 prevents the puncturing cannula 16 inserted into the groove 14 from being moved therethrough in a horizontal direction. The projection 17a of the T-shaped adapter 17 which is inserted into the groove 14 is provided at the end with a semicircular recess 17b to conform to the peripheral outline of the puncturing cannula 16. This semicircular recess 17b and the semicircular recess 14a of the end portion of the groove 14 jointly constitute a guide hole 18 for insertion of the puncturing cannula 16.

Reference numeral 19 is a connection cable to electrically connect the transducer elements 13 to a transmitting-receiving device.

There will now be described the operation of the probe 10 of this invention constructed as described above. Before diagnosis is commenced, the support 11 of the probe 10 is brought to the predetermined portion of a human body which is to be examined by scanning ultrasonic beams radiated from transducer elements 13, with the T-shaped adapter 17 inserted into the groove 14 of the support 11.

The respective groups each consisting of a plurality of adjacent transducer elements 13 are operated in turn at a high speed by a electronic switching circuit. Ultrasounds issued from the transducer elements 13 are converted into ultrasonic beams. A sectional pattern of that portion of a human body which is to be pierced by the puncturing cannula 16 is indicated on a display device (not shown). While observing the displayed sectional pattern, an operator penetrates the puncturing cannula 16 through the guide hole 18 into the desired portion of a human body. The behavior of the puncturing cannula 16 during its insertion into the human body is also indicated on the display device. After the puncturing cannula 16 reaches the target portion of the human body, contrast medium is poured into the portion by a syringe attached to the cannula 16, or part of an internal tissue is aspirated through a sucker attached to the cannula 16. Later when an operator carries out the X-ray photography of the internal tissue, the adapter 17 and the support 11 of the probe 10 are pulled in the opposite directions indicated by the arrows A, B over the surface of a human body in a horizontal direction relative to the support 11 to remove the adapter 17 from the groove 14 of the support 11. Thus, the probe 10 can be easily taken off the human body with the puncturing cannula 16 alone left at site.

With the probe 10 according to the foregoing embodiment, the direction in which the puncturing cannula 16 is inserted is determined by the guide hole 18 defined by the groove 14 and adapter 17, enabling the puncturing cannula 16 to be inserted exactly into the predetermined portion of a human body. Where the support 11 of the probe 10 and adapter 17 are pulled over the surface of a human body in a horizontal direction relative to the vertically inserted cannula 16, then the probe 10 can be easily removed from the human body without touching the puncturing cannula 16, and also without changing the position in which the puncturing cannula 16 is inserted. Therefore, the removal of the probe 10 can be quickly carried out, making it unnecessary to acquire advanced skill particularly for this purpose.

Figure 4:
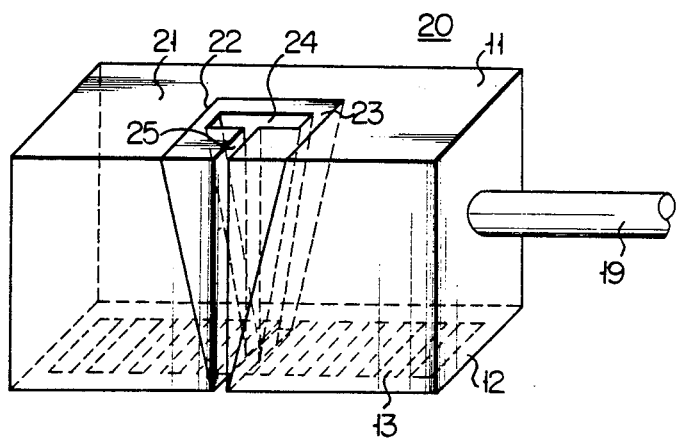
FIG. 4 is a perspective view of an ultrasound probe according to a second embodiment of the invention.
Figure 5:
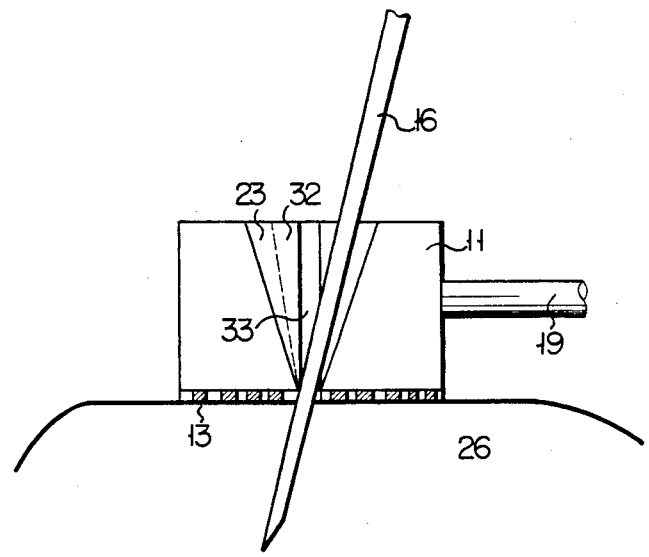
FIG. 5 is a sectional view of the ultrasound prove of FIG. 4, when put to practical use.

There will now be described another probe by reference to FIGS. 4 and 5 according to a second embodiment of this invention.

A probe 20 according to this second embodiment has the same shape, and the transducer elements 13 are arranged in the same way as in the preceding embodiment. The parts of second embodiment which are substantially the same as those of the first embodiment are denoted by the same reference numerals, detailed description thereof being omitted.

The support 11 is provided with a wedge-shaped cavity 22 which extends partly across the support 11 substantially at the center thereof. Cavity 22, is disposed substantially perpendicular to the human body-contacting side 12 of the support 11, is tapered toward said human body-contacting side 12 of the support 11, and whose top plane 21 is made flush with the upper surface of the support 11.

Detachably inserted into the wedge-shaped cavity 22 is an adapter 23 which is made of transparent material, for example, acrylic resin. The adapter 23 comprises a guide slit 24 which extends length-wise of the support 11 above the linearly arranged transducer elements 13 and is tapered toward the human body-contacting side 12 of the support 11; and a guide groove 25 which is disposed perpendicular to the guide slit 24 to allow the puncturing cannula 16 to be inserted into the support 11 from the lengthwise lateral side thereof. The lengthwise-extending guide slit 24 guides an operator in inserting the puncturing cannula 16 into the predetermined portion of a human body which is to be scanned by ultrasound beams emitted from the transducer elements 13 and also in determining the direction in which the puncturing cannula 16 is to be inserted. The guide groove 25 guides the operator in inserting the puncturing cannula 16 in a direction substantially perpendicular to the guide slit 24.

We will now describe the operation of an probe 20 according to the second embodiment having the above-mentioned construction.

That side 12 of the support 11 which is provided with the linearly arranged transducer elements 13 of the probe 20 is made to contact that portion of a human body 26 which is to be scanned by the ultrasonic beams. While the support 11 is moved, selection is made of the planigraphic image of the predetermined portion of a human body which is to be pierced by the puncturing cannula 16. This selected planigraphic image is shown on the CRT of the display device. Later, the puncturing cannula 16 is inserted into the guide groove 25 formed in the adapter 23 from the lengthwise lateral side of the support 11. In the guide slit 24, the direction is selected in which the puncturing cannula 16 is to be inserted into the predetermined portion of a human body.

A planigraphic image of the interior of the predetermined portion of a human body and also an image of the puncturing cannula 16 are indicated on the CRT of the display device. The direction in which the puncturing cannula 16 is to be inserted is visually controlled by observing an indication on the CRT. The position of that portion of the puncturing cannula 16 which is inserted into the guide slit 24 of the transparent adapter 23 can also be visually discerned. After the puncturing cannula 16 is inserted into the target portion of a human body, the support 11 is manually taken off the surface of human body with care taken to prevent the puncturing cannula 16 from touching the guide slit 24 and guide groove 25 of the adapter 23. Thereafter, the puncturing cannula 16 is penetrated into the predetermined portion of a human body, while indication on the CRT of the display device is observed.

Figure 6:
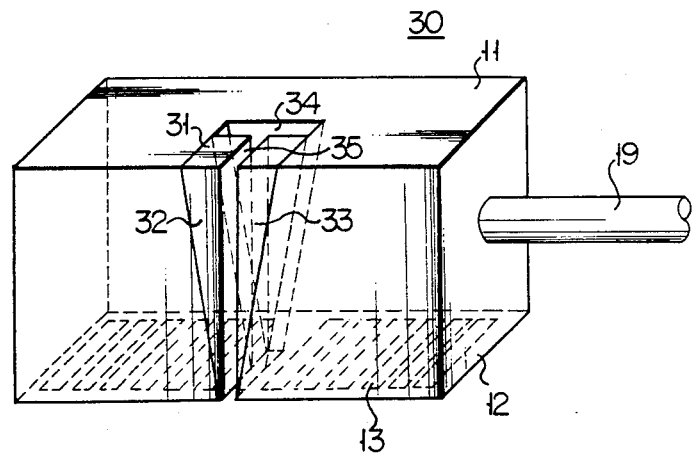
FIG. 6 is a perspective view of an ultrasound probe according to a third embodiment of the invention.

There will be described by reference to FIG. 6 a probe according to a third embodiment of this invention.

With the third embodiment, an probe 30 has the same shape and the transducer elements 13 are arranged in the same way as in the preceding embodiments. The parts of the probe 30 which are substantially the same as those of the foregoing embodiments are denoted by the same reference numerals, description thereof being omitted.

The probe 30 comprises a wedge-shaped cavity 31 similar to that of the second embodiment, which extends partly across the support 11 substantially at the center, in disposed substantially perpendicular to the human body-contacting side 12 of the support 11, is tapered toward the human body-contacting side 12 of the support 11, and whose top plane 34 is made flush with the upper surface of the support 11. Received in the wedge-shaped cavity 31 of the support 11 is a pair of first and second adapters 32 and 33 which are made of wedge-shaped transparent material, for example, acrylic resin. A guide slit 34 is defined by the aligned lateral walls of the adapters 32 and 33 and the inner lengthwise lateral wall of the wedge-shaped cavity 31 which faces the aligned lateral walls. A guide groove 35 is defined by the mutually facing walls of the adapters 32 and 33. The probe 30 of the third embodiment is operated in the same way as that of the second embodiment, description thereof being omitted.

The probes 20 and 30 of the second and third embodiments have the following advantages over the first embodiment. Since the adapter received in the probe is made of transparent material, the position of a puncturing cannula inserted into the adapter can be externally observed through the adapter. An operater can easily collate a planigraphic image indicated on the CRT of a display device with a position actually occupied by the puncturing cannula inserted into the guide slit. The other merits are that the wrong insertion of the puncturing cannula into a human body resulting from distraction or illusion on the part of an operator can be effectively avoided; the puncturing cannula is conducted in an upright position into the guide slit by being moved through the guide groove in a horizontal direction, thereby preventing the end portion of the puncturing cannula from being damaged; and the adapter made of transparent acrylic resin is inexpensive and can be easily fabricated.

We claim:

1. A probe for an ultrasonic-echo planigraphic imaging apparatus, comprising
   a support having a bottom wall adapted to be brought into contact with a human body,
   a plurality of transducer elements provided on said bottom wall and arranged at least in one row lengthwise of the support,
   said support having a cavity extending partly across the support from one lengthwise lateral wall thereof and having a wedge-shape and extending perpendicularly to the human body-contacting side of the support and being progressively tapered toward said human body-contacting side and having a top plane thereof made flush with the upper surface of the support, and
   a pair of transparent adapters separately and detachably inserted in the cavity and spaced from each other at a predetermined distance which substantially corresponds to a minimum cavity width at the bottom wall of the support, thereby defining a guide slit between the aligned lateral walls of the adapters and the inner wall of the support facing said lateral walls, and a guide groove between the mutually facing walls of the adapters to jointly constitute an opening for oblique insertion of a puncturing cannula, and for removal of the probe from the puncturing cannula while leaving the puncturing cannula pierced obliquely in the body.

2. A probe according to claim 1 wherein the transparent adapters are fabricated from an acrylic resin.

3. A probe according to claim 1 wherein the top plane of the transparent adapters received into the cavity is made flush with the upper surface of the support.

* * * * *

UNITED STATES PATENT AND TRADEMARK OFFICE
CERTIFICATE OF CORRECTION

PATENT NO. : 4,548,210

DATED : October 22, 1985

INVENTOR(S) : Susumu Enjoji and Koji Saito

It is certified that error appears in the above-identified patent and that said Letters Patent is hereby corrected as shown below:

On the title page insert

--[30] Foreign Application Priority Data

Feb. 22, 1978 [JP] ..... 18535/78

May 25, 1978 [JP] . ... 61712/78 --.

Signed and Sealed this

Fifth Day of August 1986

[SEAL]

Attest:

DONALD J. QUIGG

Attesting Officer     Commissioner of Patents and Trademarks